United States Patent [19]
Fisher et al.

[11] Patent Number: 4,567,758
[45] Date of Patent: Feb. 4, 1986

[54] APPARATUS FOR TESTING THE BOND STRENGTH OF MATERIALS

[75] Inventors: Robert K. Fisher, 3818 Delano St., Silver Spring, Md. 20902; George L. Fisher, Jr., Silver Spring, Md.

[73] Assignee: Robert K. Fisher, Silver Spring, Md.

[21] Appl. No.: 609,745

[22] Filed: May 14, 1984

[51] Int. Cl.$^4$ ............................................. G01N 3/00
[52] U.S. Cl. ..................................... 73/150 A; 73/827
[58] Field of Search ............................. 73/150 A, 827

[56] References Cited

U.S. PATENT DOCUMENTS

| 2,113,725 | 4/1938 | Goldman | 73/150 A |
| 3,433,699 | 3/1969 | Rumble | 156/580 |
| 3,628,378 | 12/1971 | Regan, Jr. | 73/798 |
| 3,741,012 | 6/1973 | Day | 73/150 A |
| 3,821,892 | 7/1974 | Saberg | 73/827 |
| 4,393,699 | 7/1983 | Seiler, Jr. | 73/150 A |
| 4,491,014 | 1/1985 | Seiler, Jr. | 73/150 A |

FOREIGN PATENT DOCUMENTS

| 1455534 | 11/1976 | United Kingdom | 73/150 A |
| 587372 | 1/1978 | U.S.S.R. | 73/150 A |

OTHER PUBLICATIONS

James F. N. Seiler, Jr., U.S. Patent Application S/N 441,310, filed Nov. 8, 1982 for "Bond Testing Apparatus".

Primary Examiner—Charles Frankfort
Assistant Examiner—W. Morris Worth
Attorney, Agent, or Firm—Mason, Fenwick & Lawrence

[57] ABSTRACT

Apparatus for testing the bond strength of materials comprising a housing having a cavity, an extrudable fluid seal received in the cavity, and a passage for placing the fluid seal in communication with a source of pressurized fluid. A material is attached to a fastener associated with the housing, coaxial with the housing's longitudinal axis. The fastener, the material being tested, and the extrusion boundary of the fluid seal are independent of the pressurized fluid applied to the fluid seal.

34 Claims, 17 Drawing Figures

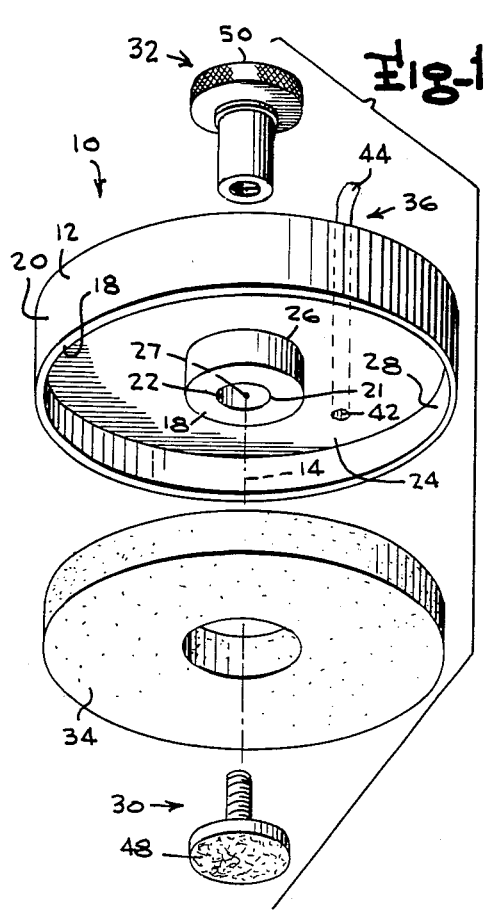
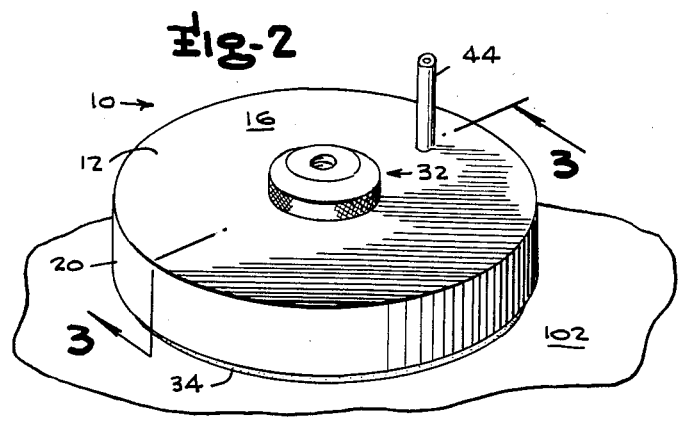
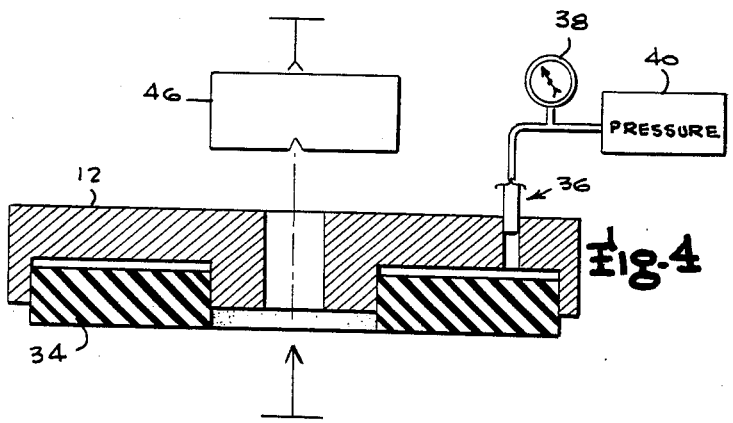
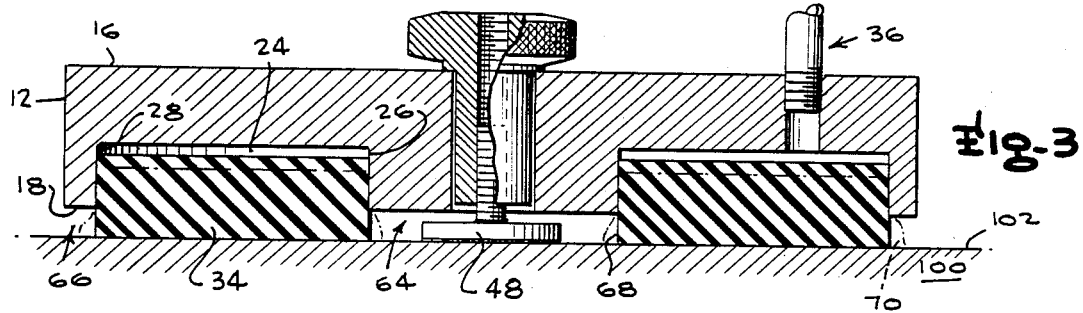
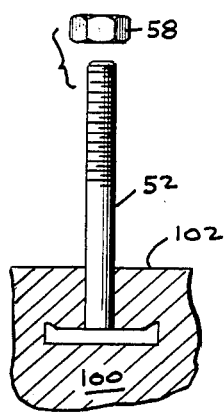
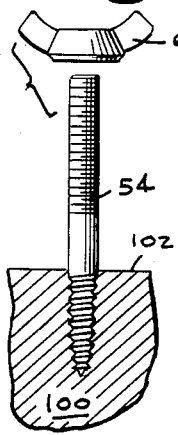
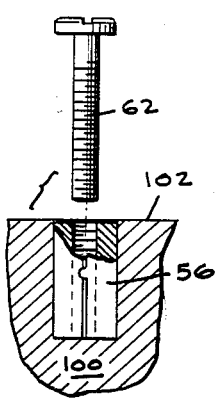
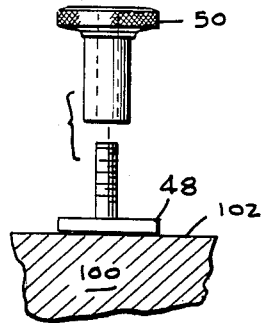

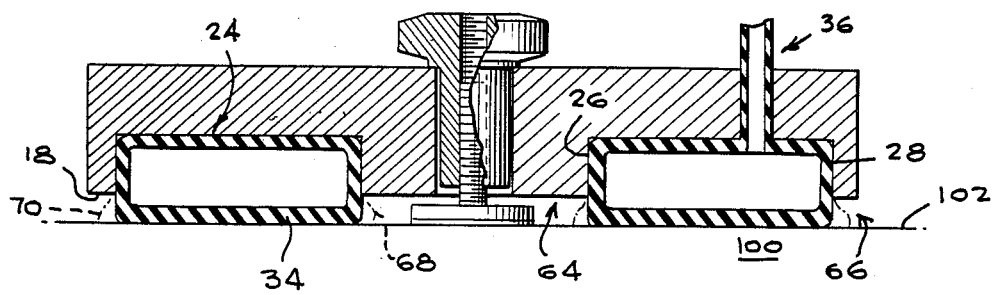
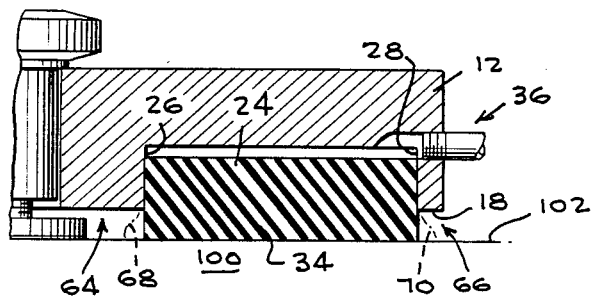
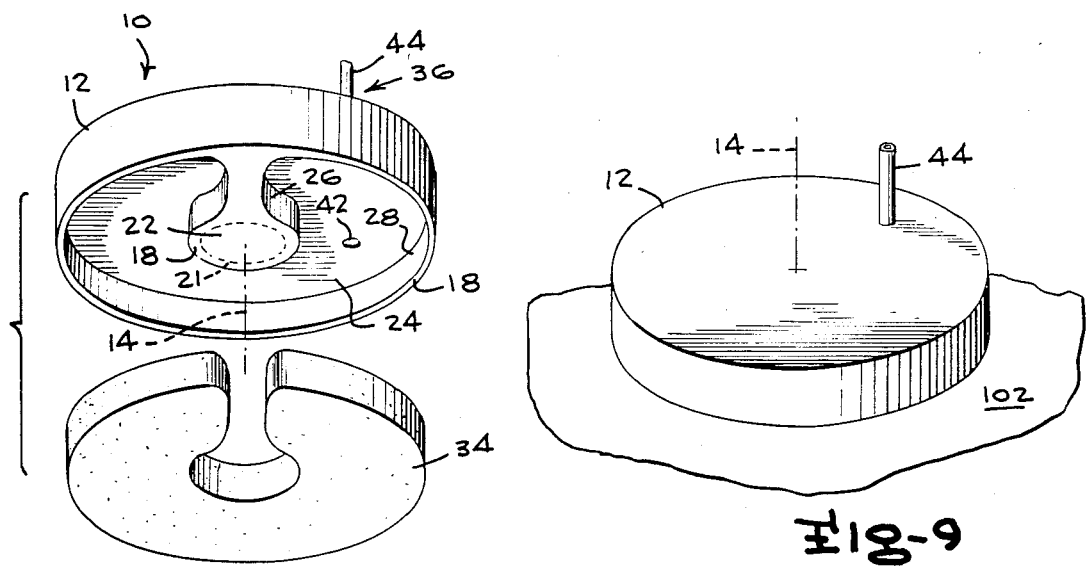

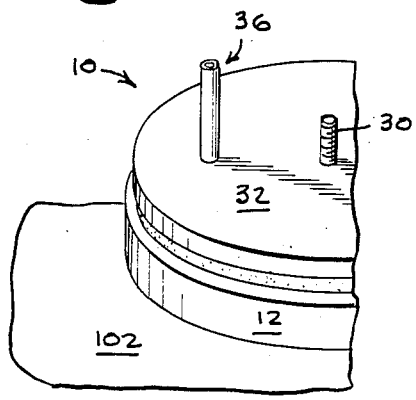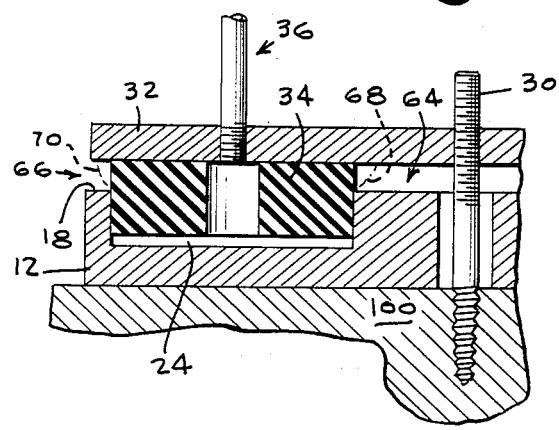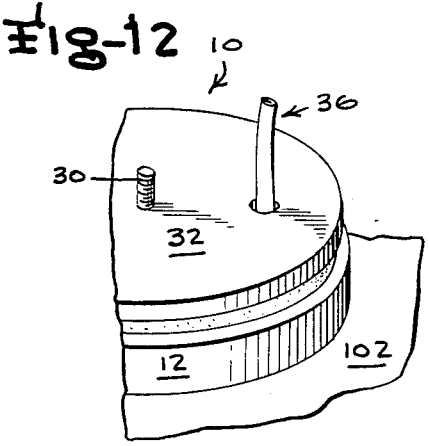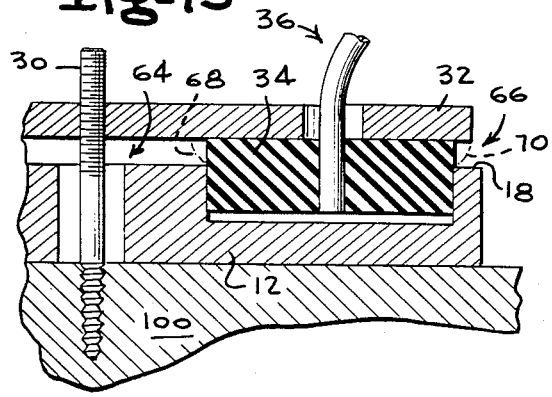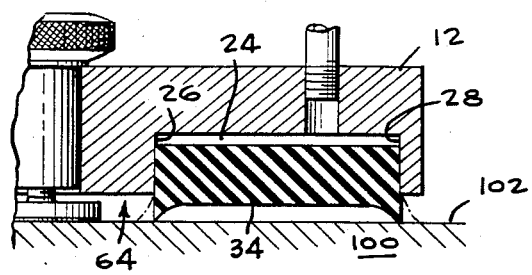

APPARATUS FOR TESTING THE BOND STRENGTH OF MATERIALS

BACKGROUND OF THE INVENTION

The present invention is directed to the field of adhesion testers, and is more specifically directed to apparatus for testing the bond strength of materials which is self aligning.

Adhesion testers which test the bond strength of a material have been made in a number of forms which operate in different ways. However, they generally have four steps in common: (1) attaching a fastener to the material to be tested, (2) applying a tensile force to the fasteners along an axis normal to the surface, (3) measuring the maximum tensile force required to cause bond failure, and (4) computing a relative measure of the bond strength by dividing the maximum tensile force by the stressed surface area of the failed bond. Although these steps appear to be simple, they are subject to the flaws and operator biases which can introduce errors into the final measurement.

The major problem encountered with respect to step (1) is the introduction of flaws into the material prior to testing. Surface flaws, particularly sharp scratches, dents, or corners constitute points of high stress concentration that are essentially pre-loaded. Pre-loading can cause premature failure at these points, which can weaken the sample and introduce shock fronts that initiate total failure, in much the same manner as a score cut in a piece of glass. A second problem is that the means for attachment must be adapted to the material and aligned perpendicular with the material surface. The adaptability of the testing apparatus is important in the testing of in-situ materials, particularly material composites having prepared fasteners.

The major problem encountered with respect to step (2) is that of introducing an uneven stress distribution over the bond area being tested. Bond failures will first occur at the areas of highest stress. The neighboring areas thereby become overloaded, resulting in premature failure of the entire sample. The major cause of uneven stress distribution is the application of off-axis loads, particularly at large distances from the surface being tested, and generally is the result of the structure of the testing device itself. The alignment of devices having attached torquing wheels, alignment feet, hand pumps, or unbalanced gimbals depends heavily upon the skill of the operator, and is therefore high susceptible to error.

The major problem encountered with respect to step (3) stems from unknown or uncontrollable variances between the actual force applied and the indicative parameter being measured. The three commonly measured parameters used to determine force are: counterbalanced masses in known gravitational fields, distances (or displacements) in conjunction with known elastic strains, and pressures in conjunction with known areas. Implicit in the measurement of any of these parameters is the assumption of some exact correlation that is both predictable and verifiable. This assumption often is not warranted because the correlation is affected by unrecognized or unmeasurable frictional losses in slidable systems such as weighted pulleys, moving springs, and constrained moving seals, and/or elastic losses and changing areas in deformable pressurized systems such as membranes and diaphragms.

The major problem encountered with step (4) is that the area of the bond failure is unpredictable and will vary from sample to sample. The force required to separate the material therefore is normalized by determining the failed bond area exposed after each test. Different tests can then be compared. This post-test interpretation of the area is normally left to the failure analyst, but some devices have attempted to define the area prior to testing by scoring the perimeter around the sample. This solution is contraindicated because it defeats the in-situ nature of the test, and gives rise to the types of problems and errors associated with step (1).

A common configuration for devices for testing the bond strength of materials is a pneumatic or hydraulic center pull jack having a conventional seal installed in a classical manner which precludes seal extrusion and requires some initial squeeze friction that increases with pressure. Devices using this configuration are shown in U.S. Pat. Nos. 2,113,725 to Goldman and 3,628,378 to Regan, Jr. These devices characterize the prior art for closed pneumatic systems having slidable sealing elements.

Goldman has the primary advantage of being capable of generating a large force along its axis by means of a relatively small pneumatic hand pump. This advantage is offset by several disadvantages. The maximum fluid pressure serves as a measure of the maximum force, but only the pressurized cross-sectional area can be well defined. The sealing elements—a leather cup seal and a common stuffing box—suffer unmitigated losses from initial squeeze friction, pressure dependent compression friction, and high variable slip-stick friction arising from transitions between the appropriate dynamic and static coefficients as the hand pump hesitates between strokes. The resolution of force required by step (3) based on pressure times area is severely compromised by these three frictional losses. Furthermore, the alignment of the axis of the device with the axis normal to the sample depends on the skill of the operator and is therefore subject to all the problems associated with step (2) which lead to premature failures and inconsistencies.

The Regan, Jr. device constitutes an improvement over the Goldman device in that it eliminates one seal (the stuffing box) and reduces the potential slip-stick friction by applying a contiuous flow of pressurized fluid through a flexible conduit. These changes reduce the alignment problems aggravated by the operation of Goldman's hand-pump. However, the Regan, Jr. device has the same initial alignment problem and suffers from the same frictional losses due to initial squeeze and pressure dependent friction of the slidable seal as the Goldman device. The Regan, Jr. patent recognizes the problem, calling the force measurement "nominal" and suggesting that "the device should be calibrated using an accurate standard." (Column 2, lines 50–52.)

A device which eliminates the slidable seals is characterized by U.S. Pat. No. 3,821,892 to Saberg. Saberg replaces the slidable seals with a deformable seal in the form of a diaphragm. The elastic losses, though ever present, are masked by the inclusion of a helical spring. However, this device suffers from a severe balance problem analogous to that of a two pound pot with a ten pound handle; i.e., the device tips over unless loaded. The gimbal then acts as a lever transferring the weight of the handle into a horizontal force on the fastener (called a dolly in the patent). A non-axial force component assures non-axial loads, premature failures, and erroneous results. Also, the diaphragm must be strong enough to prevent its extrusion into the lower chamber. Poor force alignment and elastic losses are inevitable, as are losses due to the helical spring, so that Saberg's device is incapable of accomplishing either step (2) or (3).

A device incorporating both an annular diaphragm and an annular piston is exemplified by Great Britain Pat. No. 1,455,534 to Centrum Techniki Okretowej. The annular diaphragm is secured to a plate by two annular rings forming a channel which accommodates the annular piston. When in operation, fluid pressure is contained between the plate and the diaphragm. The diaphragm is externally constrained by the inner and outer walls of the securing rings and the top surface of the annular piston. The clearance between the piston and the securing rings determines the elastic properties needed for the diaphragm. If the clearance is made large, so as to impart to the device a self-alignment capability, then the diaphragm will have to be strong enough to prevent its extrusion into the clearance, which could cause it to seize, pinch, or rupture. Conversely, if the clearance is small, then the diaphragm may be made of a thinner material that has a smaller elastic loss and a larger piston contact area. However, the device will then lose the self-alignment capability. Thus, there must be a compromise between the good alignment required by step (2) and the minimal elastic losses and area reductions required by the measurement in step (3). A careful reading of the Centrum patent (page 2, lines 95-96) indicates a preference for minimal losses that precludes the hazards of self-alignment in favor of fixed-alignment of the force "in a direction parallel to the axis of the instrument." The Centrum device is not self-aligning, and the piston may seize in the channel if the axis of both the fastener and the device are not aligned normal to the surface prior to testing.

To reduce elastic losses and obtain self-alignment, it has been proposed to apply pneumatic pressure directly to the test surface and the material fastener. Such a device is exemplified by U.S. Pat. No. 4,393,699 to Seiler, Jr. Seiler, Jr. uses an open-hole membrane peripherally secured to a plate. Air pressure initiates an hermetic seal between the membrane and the material to be tested along a line formed by the membrane hole. The gas is thus contained by four distinct surfaces: the plate, the membrane, the surface of the material being tested, and the material fastener. This device suffers from several problems. First, unmitigated losses still exist along one seal perimeter. Second, the assembly can only test materials that are sufficiently smooth, regular, and non-porous enough to permit an hermetic seal to be formed by the interface between the membrane and the material surface. Third, although this device tends to apply a tensile force in accordance with step (2), the magnitude of that force depends upon the size of the material fastener, or more precisely, upon the pressurized area within the membrane minus the actual area stressed to failure, which can only be determined after each test. Attempts to define the area by scoring the perimeter only violate step (1). Thus, a direct and verifiable force calibration via pressure measurement cannot be assigned to the device without also considering the area to be stressed. Moreover, because the membrane is open at the center, the device does not lend itself easily to direct force calibration techniques using conventional methods. The dependence of the applied tensile force upon the nebulous area stressed by the fastener, and other factors, clearly compromises the force measurement required by step (3). That error in force measurement is compounded by the computation required by step (4).

Another device exemplified by U.S. Pat. No. 4,491,014 to Seiler, Jr., employs a piston having a peripheral groove fitted with a gasket and a central open chamber for the loading fixture, which is subjected to pressure together with the gasket. This device operates according to the same principles as Seiler, Jr. U.S. Pat. No. 4,393,699, and also suffers from the same problems.

In summary, no simple "closed" pneumatic or other pressure-activated system exists for the purpose of testing the bond strength of materials, which is inherently self-aligning as well as being small, inexpensive, and suited to field service work. The "open" pneumatic systems exemplified by the above-described patents are further limited in their application to smooth, regular, non-porous materials, cannot be directly calibrated or verified and produce unpredictable forces depending on the area stressed. It is the solution of these problems to which the present invention is directed.

SUMMARY OF THE INVENTION

Therefore, it is the primary object of this invention to provide apparatus for measuring the bond strength of materials which is inherently self-aligning, and is also small, inexpensive, and suited to field service.

It is another object of this invention to provide apparatus for measuring the in-situ bond strength of materials which is adaptable to a wide variety of materials.

It is still another object of this invention to provide apparatus for measuring the bond strength of materials which can be directly calibrated and verified.

It is still another object of this invention to mitigate friction at all seal boundaries and produce a supplemental force capable of further compensating for the residual losses.

The foregoing and other objects of the invention are achieved by provision of apparatus for testing the bond strength of materials comprising a housing having a longitudinal axis perpendicular to a central area on its bottom transverse surface to or through which the material is tensively engaged, a cavity formed in the bottom transverse surface beyond the central area so that its centroid of transverse area lies on the longitudinal axis, a fluid seal received in the cavity, and fluid communication means for placing the fluid seal in fluid communication with a source of pressurized fluid and fluid pressure sensing means. The cavity formed in the housing has an inner wall and an outer wall. The inner and outer walls can intersect, for example as in a horseshoe shape, or can remain separate, for example as concentric cylinders forming an annular shape. The fluid seal is fitted to the inner and outer walls and forms its extrusion boundary along coextensive portions of the inner and outer walls when pressurized. The cavity and the central area of the housing are not in fluid communication with each other.

In one aspect of the invention, the fluid communication means comprises an inlet port either penetrating the cavity through an outer wall of the housing or penetrating the seal, and a flexible conduit connected to the inlet port.

In another aspect of the invention, a direct force measuring means can be placed in direct communication with the stressed members, intersecting the axis of the housing.

In another aspect of the invention, the fluid providing the fluid pressure is compatible with the ambient fluid, so that exposure of the pressure-providing fluid to the ambient does not constitute a hazard.

In still another aspect of the invention, the device is centrally adaptable to in-situ composites of materials having common fasteners and complementary attachment means.

A better understanding of the disclosed embodiments of the invention will be achieved when the accompanying detailed description is considered in conjunction with the appended drawings, in which like reference numerals are used for the same parts as illustrated in the different figures.

BRIEF DESCRIPTION OF THE DRAWINGS

FIG. 1 is an exploded, perspective view of a first embodiment of the invention;

FIG. 2 is an assembled, perspective view of the embodiment shown in FIG. 1;

FIG. 3 is a cross-sectional view taken along line 3—3 of FIG. 2;

FIG. 4 is a cross-sectional view of an alternate embodiment of the invention shown in FIG. 1;

FIGS. 5A-5D are partial cross-sectional views of in-situ material fasteners and attachment means for use in the appropriately adapted invention;

FIG. 6 is a cross-sectional view of a second alternate embodiment of the invention shown in FIG. 1;

FIG. 7 is a partial, cross-sectional view of a third alternate embodiment of the invention shown in FIG. 1.

FIG. 8 is an exploded, perspective view of a second embodiment of the invention;

FIG. 9 is an assembled, perspective view of the embodiment shown in FIG. 8.

FIG. 10 is a partial assembled, perspective view of a third embodiment of the invention;

FIG. 11 is a cross-sectional view taken along line 11—11 of FIG. 10;

FIG. 12 is a partial assembled, perspective view of an alternate embodiment of the invention shown in FIG. 11;

FIG. 13 is a cross-sectional view taken along line 13—13 of FIG. 12; and

FIG. 14 is a partial, cross-sectional view of a fourth alternative embodiment of the invention shown in FIG. 1.

DESCRIPTION OF THE PREFERRED EMBODIMENTS

Referring now to FIGS. 1-3, there is illustrated a first embodiment of apparatus for measuring the bond strength of materials comprising a pressure-activated ram generally designated by the reference numeral 10, for use on a material 100 having a surface 102.

Ram 10 comprises a cylindrical housing 12 having a longitudinal axis 14, a top transverse surface 16, a bottom transverse surface 18, and a peripheral side wall 20. An adaptable central volume, illustrated in FIGS. 1-3 as a central bore 22, extends from the central area 21 of bottom transverse surface 18 through housing 12 coaxial with longitudinal axis 14. An annular peripheral cavity 24 having an inner wall 26 and an outer wall 28 is formed in the bottom transverse surface 18 of housing 12 beyond central area 21, so that its centroid of transverse area 27 lies on the axis 14. It should be understood that such designations as top, bottom, and longitudinal are arbitrary, bottom referring to the surface of ram 10 in which cavity 24 is formed, and longitudinal referring to the dimension of ram 10 perpendicular to its bottom.

Housing 12 can be made from any machinable metal, plastic, or other material commonly used with pressurized fluids and capable of supporting the loads developed. Stainless steel and aluminum are two examples of such materials.

Ram 10 further comprises a gripping means 32 received in central bore 22 for securing the material, structure, or fastener whose strength is being tested. Gripping means 32 is aligned coaxially with axis 14 and cooperates with housing 12 for engaging material fastener 30 on or through central area 21 of central bore 22 coaxial with axis 14 of housing 12. An annular fluid seal 34 received in cavity 24 is fitted to compress against inner and outer walls 26 and 28, and form its extrusion boundary along coextensive portions of inner and outer walls 26 and 28. Cavity 24 and fluid seal 34 need not be annular in shape. Cavity 24 can, for example, be horseshoe-shaped, as illustrated in FIG. 8, with its inner and outer walls 26 and 28 intersecting. Fluid seal 34 then has a corresponding horse-shoe shape, as further illustrated in FIG. 8.

Clearance tolerances can be kept to nearly zero for any cavity shape (annulus, horseshoe, etc.) by molding seal 34 in place using a low modulus elastomer. A properly fitted seal will bulge when pressurized against outwardly diverging areas of the walls 26 and 28 within the cavity 24, or against the peripheral edges of the cavity 24, or both. Thus, commercially available compression and lip seals, as shown in FIG. 14, as epitomized by O-rings and U-cup packings, can be used, as well as ported hollow seals which can be fluid-filled, as shown in FIG. 6, if properly fitted to extrude protuberantly when pressurized.

Fluid communication means 36 is associated with housing 12 for placing seal 34 in fluid communication with fluid pressure sensing means 38 and a source of pressurized fluid 40. Preferably, the fluid providing the fluid pressure is compatible with its ambient, e.g. oil in oil, water in water, or a non-toxic gas in air. Fluid communication means 36 can comprise an inlet port 42 penetrating cavity 24 through an outer wall of housing 12—for example through top transverse surface 16 of housing 12, as illustrated in FIGS. 1-4; through side wall 20, as illustrated in FIG. 7; or through the seal 34, as illustrated in FIGS. 11 and 13—and a flexible conduit 44 connected to inlet port 42. In the case of a ported hollow seal, the port 42 is integral with seal 34, as illustrated in FIG. 6. During testing, the material 100 is independent of the pressurized fluid applied to fluid seal 34, i.e., the material 100 is not in fluid communication with the source of pressurized fluid 40.

As illustrated in FIGS. 1-3, housing 12 is adapted to test the composite strength of material 100 in bond with fastener 30, which comprises a threaded stub 48 bonded to surface 102 in FIG. 5D, where gripping means 32 comprises a knurled thumb nut 50. Depending upon the material to be tested, and because of the in-situ nature of the test, housing 12 must be adapted to the test structure rather than vice versa. When properly adapted, common in-situ composites of a fastener 30 and a material 100, such as an anchor 52 in concrete, a wood-to-machine screw 54 in wood, or an expansion nut 56 in plaster can be attached to housing 12 simply by using their respective attachment means as grips 32 which can comprise a hex nut 58, a wing nut 60, or a simple screw 62. For these cases the central volume of housing 12 is bored out to form central bore 22. When the central volume is removed, housing 12 can be inverted as illustrated in FIGS. 10-13, so that seal 34 presses upwardly against any gripping means 32 having a transverse dimension spanning the seal, such as a threaded plate, washer, etc.

When ram 10 is to be used solely with a specific material fastener 30, gripping means 32 can be incorporated into housing 12 by threading or otherwise adapting the central volume to accommodate it. Alternatively, the central volume can be left intact, as shown in FIGS. 8 and 9, and material 100 can be tested directly simply by adhering surface 102 to central area 21 of bottom transverse surface 18. Here the grip comprises the surface of central area 21, and the fastener comprises an adhesive, which may be the material 100. In fact, the only requirement for attaching ram 10 to a material 100 is that the attachment be centered on axis 14.

Direct force measuring means 46 can be placed in direct communication with the stressed members, for example with material fastener 30 and gripping means 32, intersecting axis 14 of housing 12 as illustrated in FIG. 4, or with material fastener 30 and the central volume. Measuring means 46 can be used instead of, or in addition to, sensing means 38. Both sensing means 38 and measuring means 46 can be strain or displacement responsive devices of the kind well-known in the art, such as strain gauges, spring scales, electrical transducers, mass balances, etc.

In use, the in-situ testing of a material 100 is begun by putting fluid seal 34 in cavity 24 and centering the appropriate gripping means 32 and fastener 30 on axis 14 of housing 12, so that fluid seal 34 is confined to the cavity 24 when gripping means 32 and fastener 30 are loosely connected together. Fluid pressurization means 40 is used to slowly pressurize the fluid and fluid seal 34 by way of fluid communication means 36. The fluid pressure forces seal 34 into contact with surface 102, as shown in FIGS. 3, 6, and 7, or with gripping means 32, as shown in FIGS. 11 and 13, at which point seal 34 begins to bulge and form its extrusion boundary via radial expansion against inner and outer walls 26 and 28 of cavity 24. Because cavity 24 is formed in housing 12 so that its centroid of transverse area lies on axis 14, the increasing pressure forces gripping means 32 into coaxial tension with material fastener 30, thereby aligning the force on material fastener 30 perpendicular to surface 102.

As illustrated in FIGS. 3, 6, 7, and 13, as the fluid pressure continues to increase, the interal pressure of fluid seal 34 causes it to bulge along any surface in contact with the ambient and thus extrude into the inner and outer spaces 64 and 66 between bottom transverse surface 18 of housing 12 and surface 102 of material 100 or gripping means 32. Inner and outer bulged surfaces 68 and 70 are thus formed at the extruded edges of seal 34, and are held in tension by the internal seal pressure acting in a direction outwardly normal to each surface 68 and 70. The tension along these expanded surfaces pulls against the points of seal 34 held in frictional contact along inner and outer walls 26 and 28 of cavity 24. The effect of pre-stressing these points of frictional contact is to reduce the amount of residual force required to initiate and sustain motion between seal 34 and cavity 24, which is, by definition, the friction. Furthermore, the internal seal pressure at curved surfaces 68 and 70 contributes an additional force component in the direction of motion by pressing against the edges or outwardly diverging surfaces of walls 26 and 28. The magnitude of this additional force increases with pressure, as does the residual friction, thereby giving rise to a self-compensating device whose total load transfer qualities are dependent only upon the elastic properties, transverse area, and peripheral interaction of seal 34 with cavity 24. Hence, a primary force is developed by the fluid pressure acting across the transverse area of seal 34, while a secondary force is developed by the bulging seal's interaction with the cavity perimeter, which acts counter to the friction produced and mitigated along that same perimeter. By varying these parameters, the device can produce a net force on gripping means 32 in excess of the fluid pressure times the transverse of fluid contact across seal 34, which is predictable and verifiable by direct force measuring means 46 or other means.

As the fluid pressure from pressurization means 40 is increased, sensing means 38 is monitored, and its peak value recorded when the material 100 and fastener 30 tear apart. The maximum force is then determined from the peak value via calibration chart, curve, etc. The stressed area of the failed surface is also measured. Both values are recorded and their ratio computed as a relative measure of the strength of the fastener 30, or material 100, or the interface between them, depending upon where the failure occurs.

Thus, it will be seen that all embodiments of the present invention provide a unique method for testing the bond strength of materials. While preferred embodiments of the invention have been disclosed, it should be understood that the spirit and scope of the invention is to be limited solely by the appended claims, since numerous modifications of the disclosed embodiments will undoubtedly occur to those of skill in the art.

We claim:

1. Apparatus for testing the bond strength of materials, comprising:

a housing having a longitudinal axis, a top transverse surface, a bottom transverse surface, said bottom transverse surface including a central area, said longitudinal axis extending through the center of said central area and perpendicular to said bottom transverse surface, a central axial volume extending through said housing coaxial with said longitudinal axis, and a cavity formed in said bottom transverse surface beyond said central area and having an inner wall, an outer wall, and a centroid of transverse area, said inner wall and said outer wall each having a surface and a bottom edge, and said centroid of transverse area of said cavity lying on said longitudinal axis;

attachment means coaxial with said longitudinal axis and cooperating with said housing for engaging the material being tested;

a fluid seal received in said cavity and adapted to extrude protuberantly from said cavity when fluid pressure is applied thereto, said fluid seal forming its extrusion boundary along coextensive portions of said inner and outer walls; and fluid communication means for placing a portion of said fluid seal in fluid communication with a source of pressurized fluid; the material being tested, said attachment means, and the extrusion boundary of said fluid seal being independent of the pressurized fluid, whereby internal seal pressure at the extrusion boundary of said fluid seal contributes an additional force component in the direction of motion by pressing against the edges or surfaces of said inner and outer walls.

2. The apparatus of claim 1, wherein said housing is cylindrical and said seal is annular.

3. The apparatus of claim 1, wherein said seal is horse-shoe shaped.

4. The apparatus of claim 1, wherein said fluid seal is molded in place in said cavity using a low modulus compound.

5. The apparatus of claim 2, wherein said fluid seal comprises a compression seal.

6. The apparatus of claim 2, wherein said fluid seal comprises a lip seal.

7. The apparatus of claim 1, wherein said fluid seal comprises a ported hollow seal.

8. The apparatus of claim 1, wherein said fluid communication means comprises an inlet port penetrating said housing to communicate with said cavity and a conduit connected to said inlet port.

9. The apparatus of claim 1, said attachment means comprising a material fastener received in said central volume.

10. The apparatus of claim 9, wherein the transverse dimension of said attachment means spans said fluid seal.

11. The apparatus of claim 9, said attachment means further comprising gripping means cooperating with said housing for engaging said material fastener.

12. The apparatus of claim 1, said attachment means comprising said central area.

13. The apparatus of claim 1, wherein said fluid communication means comprises an inlet port penetrating said fluid seal.

14. The apparatus of claim 1, wherein said fluid seal is adapted to compress radially and form a fluid sealing line by means of radial expansion against said inner and outer walls of said cavity when subjected to fluid pressure.

15. Apparatus for testing the bond strength of materials, comprising:
    means for securing the material whose strength is being tested, the material having a surface;
    means for applying a tensile force to said securing means along an axis normal to the surface of the material, said tensile force applying means including a cavity formed therein, said cavity having an inner wall, an outer wall, and a centroid of transverse area, said inner wall and said outer wall each having a surface and a bottom edge, and said centroid of transverse area lying on said axis normal to the surface of the material;
    means located in said cavity of said tensile force applying means for aligning the tensile force on said securing means perpendicular to the surface of the material and for drawing said tensile force applying means away from the material, said aligning and drawing means adapted to extrude protuberantly from said cavity when fluid pressure is applied thereto and forming a fluid tight seal with said tensile force applying means and forming its extrusion boundary along coextensive portions of said inner and outer walls of said cavity, said securing means being positioned centrally of said aligning and drawing means; and
    means for applying a pressurized fluid to said aligning and drawing means, whereby said aligning and drawing means aligns the axis of said apparatus perpendicular to the surface of the material and draws said tensile force applying means away from the material; said securing means, the extrusion boundary of said aligning and drawing means, and the material being independent of the pressurized fluid, whereby internal pressure in said aligning and drawing means at the extrusion boundary thereof contributes an additional force component in the direction of motion by pressing against the edges or surfaces of said inner and outer walls.

16. Apparatus for testing the bond strength of materials, comprising:
    a cylindrical housing having a longitudinal axis, a bottom transverse surface, said longitudinal axis being perpendicular to said bottom transverse surface, and an annular cavity formed in said bottom transverse surface having an inner wall, an outer wall, and a centroid of transverse area, said inner wall and said outer wall each having a surface and a bottom edge, and said centroid of transverse area of said cavity lying on said longitudinal axis;
    a material fastener received in said housing coaxial with said longitudinal axis and cooperating with said housing for engaging the material being tested;
    an annular fluid seal received in said cavity and adapted to extrude protuberantly from said cavity when fluid pressure is applied thereto, said fluid seal forming its extrusion boundary along coextensive portions of said inner and outer walls; and
    fluid communication means for placing a portion of said fluid seal in fluid communication with a source of pressurized fluid; said material fastener, the extrusion boundary of said fluid seal, and the material being tested being independent of the pressurized fluid, whereby internal seal pressure at the extrusion boundary of said fluid seal contributes an additional force component in the direction of motion by pressing against the edges or surfaces of said inner and outer walls.

17. The apparatus of claim 15, wherein said cavity is annular.

18. The apparatus of claim 15, wherein said cavity is horse-shoe shaped.

19. The apparatus of claim 15, wherein said aligning and drawing means comprises a fluid seal molded in place in said cavity using a low modulus compound.

20. The apparatus of claim 19, wherein said fluid seal comprises a compression seal.

21. The apparatus of claim 19, wherein said fluid seal comprises a lip seal.

22. The apparatus of claim 15, wherein said aligning and drawing means comprises a ported hollow fluid seal.

23. The apparatus of claim 15, wherein said fluid pressure applying means comprises inlet means penetrating said tensile force applying means to communicate with said cavity and conduit means connected to said inlet means.

24. The apparatus of claim 15, wherein said fluid pressure applying means comprises an inlet port penetrating said fluid seal.

25. The apparatus of claim 15, wherein said aligning and drawing means is adapted to compress radially and form a fluid sealing line by means of radial expansion against said inner and outer walls of said cavity when subjected to fluid pressure.

26. The apparatus of claim 16, wherein said fluid seal is molded in place in said cavity using a low modulus compound.

27. The apparatus of claim 26, wherein said fluid seal comprises a compression seal.

28. The apparatus of claim 26, wherein said fluid seal comprises a lip seal.

29. The apparatus of claim 16, wherein said fluid seal comprises a ported hollow seal.

30. The apparatus of claim 16, wherein said fluid communication means comprises an inlet port penetrating said housing to communicate with said cavity and a conduit connected to said inlet port.

31. The apparatus of claim 16, wherein the transverse dimension of said material fastener spans said fluid seal.

32. The apparatus of claim 16, further comprising gripping means cooperating with said housing for engaging said material fastener.

33. The apparatus of claim 16, wherein said fluid communication means comprises an inlet port penetrating said fluid seal.

34. The apparatus of claim 16, wherein said fluid seal is adapted to compress radially and form a fluid sealing line by means of radial expansion against said inner and outer walls of said cavity when subjected to fluid pressure.

* * * * *